US009475836B2

United States Patent
Wang et al.

(10) Patent No.: US 9,475,836 B2
(45) Date of Patent: Oct. 25, 2016

(54) PROTOPANOXADIOL DERIVATIVE, PREPARATION METHOD THEREOF AND APPLICATION THEREOF

(71) Applicant: SHANG HAI INNOVATIVE RESEARCH CENTER OF TRADITIONAL CHINESE MEDICINE, Shanghai (CN)

(72) Inventors: Jihua Wang, Shanghai (CN); Shoufu Lu, Shanghai (CN); Changjiang Xu, Shanghai (CN); Zirong Yang, Shanghai (CN)

(73) Assignee: Shang Hai Innovative Research Center of Traditional Chinese Medicine, Shanghai (CN)

( * ) Notice: Subject to any disclaimer, the term of this patent is extended or adjusted under 35 U.S.C. 154(b) by 0 days.

(21) Appl. No.: 14/764,543

(22) PCT Filed: Jan. 26, 2014

(86) PCT No.: PCT/CN2014/071500
§ 371 (c)(1),
(2) Date: Jul. 29, 2015

(87) PCT Pub. No.: WO2014/117700
PCT Pub. Date: Aug. 7, 2014

(65) Prior Publication Data
US 2015/0368289 A1   Dec. 24, 2015

(30) Foreign Application Priority Data
Jan. 31, 2013   (CN) .......................... 2013 1 0038993

(51) Int. Cl.
*C07J 17/00*   (2006.01)
*C07J 9/00*   (2006.01)
*A61K 31/58*   (2006.01)
*A61K 31/575*   (2006.01)

(52) U.S. Cl.
CPC .............. *C07J 17/00* (2013.01); *A61K 31/575* (2013.01); *A61K 31/58* (2013.01); *C07J 9/00* (2013.01)

(58) Field of Classification Search
None
See application file for complete search history.

(56) References Cited

U.S. PATENT DOCUMENTS 8,148,354 B2   4/2012   Hui et al.

FOREIGN PATENT DOCUMENTS

| CN | 1895256 A | 1/2007 |
|---|---|---|
| CN | 102018716 A | 4/2011 |
| CN | 102731603 A | 10/2012 |

OTHER PUBLICATIONS

Cuijpers et al. (JAMA, Mar. 14 2012, vol. 307, No. 10).*
Vieta et al. (CNS Drugs, 2013, 27: 515-529).*
Changjiang, Xu et al., 20(S)-protopanaxadiol, an active ginseng metabolite, exhibits strong antidepressant like effects in animal tests, *Progress in Neuropsychopharmacology & Biological Psychiatry* (2010), doi: 10.1016/j.pnpbp.2010.07.010.

* cited by examiner

*Primary Examiner* — Anna Pagonakis
(74) *Attorney, Agent, or Firm* — Knobbe Martens Olson & Bear LLP

(57) ABSTRACT

The present invention provides a protopanoxadiol derivative of structural formula I or II, a preparation method and an application thereof. The present invention performs structural modification on protopanoxadiol, and obtains multiple novel compounds with unique structures. As confirmed in vivo pharmacological experiments, these compounds have stronger anti-depression activity, can be used as an active ingredient in preparing medicine for preventing or treating depression-type mental illness, and have wide use and development prospect, 14 Claims, 8 Drawing Sheets

PROTOPANOXADIOL DERIVATIVE, PREPARATION METHOD THEREOF AND APPLICATION THEREOF

TECHNICAL FIELD

The present invention relates to a panoxadiol compound, specifically, to a protopanoxadiol derivative, preparation method thereof and application thereof in medicine field, and belongs to the technical field of medicine.

BACKGROUND ART

Depressive disorder, a disease manifested as depression, belongs to the scope of emotional mental disorder in mental diseases. The manifestation of depressive disorder can be summarized as "three lowness", i.e. low emotion, slow thinking and low spirits. The core symptom of depressive disorder is low emotion, and the psychological symptoms are anxiety, self-accusation, self-guilt, delusion or hallucination, attention and memory deterioration, suicidal tendency, etc.; and the somatization symptoms thereof are sleep disorder, reduced appetite, body weight loss, sexual hypoactivity, dispiritedness and lassitude, etc. Depressive disorder is a common and frequently-occurring disease threatening human health. In China, the morbidity of emotional mental diseases is 0.76%. The morbidity of depressive disorder is very high, however, the pathogenesis thereof is still not known clearly now. A conventional viewpoint is that the pathogenesis of depressive disorder is related to the abnormity of intracerebral monoamine neurotransmitters, including 5-HT(5-hydroxytryptamine), acetyl choline and catecholamines, noradrenaline and epinephrine.

In 1950s, the first developed antidepressant was monoamine oxidase inhibitor, which was replaced by tricyclic antidepressant due to severe toxic and side effects, and the latter become the first-line drug for depressive disorder treatment worldwide in 1950s. The development of selective 5-HT(5-hydroxytryptamine) reuptake inhibitor (SSRI) is compelling in recent years, and has superior pharmacokinetic and pharmacodynamic characteristics, as well as good therapeutic effect, small toxic and side effects, simple administration and fast development. However, Most of these drugs, due to their characteristics, have certain side effect on central nervous system and vegetative nervous system with gastrointestinal tract reaction.

20(S)-protopanoxadiol is one of the most important aglycones of protopanaxadiol ginsenosides, and ZL 200610027507.1 discloses the application of 20(S)-protopanoxadiol in inhibition of depression, but the effect thereof still needs to be further improved. If an improved protopanoxadiol derivative with a unique structure which shows stronger anti-depression pharmacological activity in pharmacological experimental results, is developed, it will have wide development and application prospect in preparation of drugs for preventing or treating depression mental diseases.

DESCRIPTION OF THE INVENTION

The purpose of the present invention is to provide an improved protopanoxadiol derivative with a unique structure.

Another purpose of the present invention is to provide a preparation method for the protopanoxadiol derivative.

Still another purpose of the present invention is to provide the use of the protopanoxadiol derivative in the preparation of drugs for preventing or treating depression mental diseases.

In order to realize the purposes of the present invention, the present invention provides a protopanoxadiol derivative of a structural formula I or II, the structural formula being:

Wherein, $R_1$ is —OH, =NOH or —NH$_2$; $R_2$ is —OH, =NOH or —NH$_2$; and $R_1$ and $R_2$ are not —OH simultaneously.

Preferably, when $R_1$ is —OH, $R_2$ is =NOH or —NH$_2$, or when $R_2$ is —OH, $R_1$ is =NOH or —NH$_2$.

Preferably, $R_1$ and $R_2$ each independently is =NOH or —NH$_2$.

Most preferably, $R_1$ and $R_2$ are =NOH or —NH$_2$ simultaneously.

Most preferably, $R_1$ is —OH, and $R_2$ is =NOH or —NH$_2$.

The protopanoxadiol derivative of the structural formula I or II according to the present invention is prepared by a method comprising the following steps:

1) subjecting protopanoxadiol or Adama-20S-24(R,S)-epoxy-3β,12β,25-triol to oxidation reaction to obtain a monoxide or dioxide derivative respectively; and 2) then subjecting the monoxide or dioxide derivative obtained in step 1) and hydroxylamine hydrochloride to addition reaction or further reduction reaction to obtain a compound represented by formula (I) or (II).

The dioxide derivative is:

Compound III or

Compound IV

The monoxide derivative is:

Compound V or

Compound VI

In step 1), the oxidant used during oxidation reaction is one or more of manganese dioxide, potassium permanganate, Dess-Martin reagent, PCC (pyridinium chlorochromate), PDC (pyridinium dichromate) and Jones reagent.

In step 2), the reductant used during reduction reaction is one or more of $NaBH_4$, $LiAlH_4$, Na/n-propanol and Zn/AcOH reagent.

It has been proved through experiments that the protopanoxadiol derivative of formula I or II according to the present invention exhibited stronger anti-depression activity, as compared to protopanoxadiol, and can be used as the active ingredient of an anti-depression drug.

The present invention relates to the use of the protopanoxadiol derivative having the structure of compound I or compound II in the preparation of drugs for preventing or treating depression mental diseases.

The depression mental diseases include paralepsy and recurrent depressive disorder, bipolar affective disorder and persistent mood disorder.

The depression mental diseases can be classified into three types: mild, moderate and severe types according to the symptoms upon onset of the diseases.

One or more of the protopanoxadiol derivatives of structural formula I or II as active ingredients can be formulated with one or more pharmaceutically acceptable carriers into pharmaceutical preparations according to conventional methods in medicine field.

The pharmaceutical preparation may be any preparation in the art, such as oral preparation or injection preparation.

The oral preparation may be capsule, table, pill or granule, preferably capsule.

The content of protopanoxadiol derivative as active ingredient in the pharmaceutical preparation can be determined according to the usage amount.

The carrier comprises conventional stabilizer, filler, binder, lubricant, disintegrating agent, absorption promoter, surfactant, suspending aid, wetting agent, solvent or flavoring agent in medicine field.

The stabilizer is selected from parabens such as methylparaben, ethylparaben or propylparaben; alcohols such as chlorobutanol, benzyl alcohol or phenethyl alcohol; benzalkonium chloride; phenols such as phenylphenol or methylphenol; thiomersalate; acetic anhydride; or sorbic acid, etc.

The filler is selected from starch, sucrose, lactose, mannitol, sorbitol, xylitol, microcrystalline cellulose or glucose, etc.

The binder is selected from cellulose derivatives, alginate, gelatin or polyvinylpyrrolidone, etc.

The lubricant is selected from stearic acid, polyethylene glycol, calcium carbonate, sodium hydrogen carbonate, superfine silica powder, talcum powder or magnesium stearate, etc.

The disintegrating agent is selected from microcrystalline cellulose, sodium carboxymethyl starch, crosslinked polyvinylpyrrolidone, low-substituted hydroxypropyl cellulose or crosslinked sodium carboxymethylcellulose, etc.

The surfactant is selected from sodium dodecyl benzene sulfonate, stearic acid, polyoxyethylene-polyoxypropylene copolymer, fatty acid sorbitan or polysorbate (Tween), etc.

The suspending aid is selected from superfine silica powder, beewax, cellulose or solid polyethylene glycol, etc.

The wetting agent is selected from glycerol, Tween-80, ethoxy hydrogenated castor oil or lecithin, etc.

The solvent is selected from ethanol, liquid polyethylene glycol, isopropanol, Tween-80, glycerol, propylene glycol or vegetable oil, and the vegetable oil is selected from soybean oil, castor oil, peanut oil or blend oil, etc.

The flavoring agent is selected from aspartame, sucralose, essence, citric acid or soluble saccharin, etc.

The present invention also relates to the use of a pharmaceutical preparation containing the protopanoxadiol derivative of above structural formula I or II in preparation of drugs for preventing or treating depression mental diseases.

The depression mental diseases include paralepsy and recurrent depressive disorder, bipolar affective disorder and persistent mood disorder.

The depression mental diseases can be classified into three types: mild, moderate and severe types according to the symptoms upon onset of the diseases.

The present invention showed in pharmacological experiment researches that the protopanoxadiol derivative of structural formula I or II can obviously shorten the tail suspension immobility time of mice in a classical depression model—"mice tail suspension test"; obviously shorten non-swimming time of mice in "mice forced swimming model test"; and significantly improve sucrose water intake of rats in CUMS test, indicating that the protopanoxadiol derivative of the present invention has significant anti-depression activity and has potential pharmaceutical value for treatment of depression mental diseases.

In summary, various new compounds with unique structures are obtained by structural modification on protopanoxadiol in the present application. It is proved via in-vivo pharmacological experiments that these compounds exhibit stronger anti-depression activity under lower administration dosage as compared to a positive control drug, can be used as the active ingredients in preparing drugs for preventing or treating depression mental diseases, and have wide application and development prospect.

EXAMPLES

Following examples are described for illustrating the present invention, but are not intended to limit the scope of the present invention.

The materials used in the present invention are all commercially available conventional materials, and the operation methods unmentioned are also conventional methods in the art.

Example 1

Preparation of Protopanoxadiol Derivative of Structural Formula (I) ($R_1$ and $R_2$ are =NOH)

10 g of 20(S)-protopanoxadiol (Shanghai Innovative Research Center of Traditional Chinese Medicine) was accurately weighed, and dissolvedin anhydrous dichloromethane 250 ml. PDC (pyridinium dichlorochromate) 20 g was added with stirring, thereafter stirred at room temperature for 24 h. After the completion of the reaction, the reaction solution was filtered through celite. The organic phase was concentrated to dryness, and silica gel column chromatography was performed using ethyl acetate and petroleum ether of 1:10-1:5 (volume ratio) as eluting agent, to obtain 6.4 g of compound III (purity: 95%).

Compound III

The structure was determined by ESI-MS and NMR, and the determined physicochemical data of the compound of formula (III) are as follows:

ESI-MS m/z: 457.4 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 24H), 2.85-2.95 (m, 1H), 5.10-5.14 (m, 1H).

5 g of the compound III was accurately weighed and dissolved in anhydrous methanol 100 ml. Triethylamine 2.77 g and hydroxylamine hydrochloride 1.9 g were added with stirring. The solid began to separate out after stirring at room temperature for 24 h. The reaction solution was filtered with filter paper after the completion of the reaction, and dried to obtain 4.8 g of compound (I) ($R_1$ and $R_2$ are =NOH) (purity: 95%).

The structure was determined by ESI-MS and NMR, and the determined physicochemical data of the compound of formula (I) ($R_1$ and $R_2$ are =NOH) are as follows:

ESI-MS m/z: 487.4 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 23H), 2.85-2.95 (m, 2H), 5.10-5.14 (m, 1H).

Example 2

Preparation of Protopanoxadiol Derivative of Structural Formula (I) ($R_1$ and $R_2$ are —NH$_2$)

3 g of the compound I ($R_1$ and $R_2$ are =NOH) from Example 1 was accurately weighed and dissolved in anhydrous tetrahydrofuran 50 ml. lithium aluminum hydride 0.5 g was added with stirring. After stirring at 80° C. for reaction for 3 h, the reaction solution was filter through celite after TLC showed that the reaction was completed, and the organic phase was concentrated to dryness, and silica gel column chromatography was performed using dichloromethane and methanol of 20:1-5:1 (volume ratio) as eluting agent, to obtain 1.2 g of compound I ($R_1$ and $R_2$ are —$NH_2$) (purity: 95%)

The structure was determined by ESI-MS and NMR, and the determined physicochemical data of the compound of formula (I) ($R_1$ and $R_2$ are —$NH_2$) are as follows:

ESI-MS m/z: 459.3 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 25H), 3.09 (m, 1H), 3.39 (m, 1H), 5.10-5.14 (m, 1H).

Example 3

Preparation of Protopanoxadiol Derivative of Structural Formula (I) ($R_1$ is —OH, and $R_2$ is =NOH)

10 g of 20(S)-protopanoxadiol (Shanghai Innovative Research Center of Traditional Chinese Medicine) was accurately weighed, and dissolved in anhydrous dichloromethane 250 ml. PDC (pyridinium dichlorochromate) 10 g was added with stirring, thereafter stirred at room temperature for 24 h. After the completion of the reaction, the reaction solution was filtered through celite, the organic phase was concentrated to dryness, and silica gel column chromatography was performed using ethyl acetate and petroleum ether of 1:10-1:5 (volume ratio) as eluting agent, to obtain 3.4 g of compound V (purity: 95%).

Compound V

The structure was determined by ESI-MS and NMR, and the determined physicochemical data of the compound of formula (V) are as follows:

ESI-MS m/z: 459.4 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 23H), 2.85-2.95 (m, 2H), 3.59 (m, 1H), 5.10-5.14 (m, 1H).

3 g of the compound V was accurately weighed and dissolved in anhydrous methanol 100 ml. Triethylamine 2.77 g and hydroxylamine hydrochloride 0.5 g were added with stirring. The solid began to separate out after stirring at room temperature for 24 h. The reaction solution was filtered with filter paper after the reaction was completed, and dried to obtain 1.8 g of compound (I) ($R_1$ is —OH, and $R_2$ is =NOH).

The structure was determined by ESI-MS and NMR, and the determined physicochemical data of the compound of formula (I) ($R_1$ is —OH, and $R_2$ is =NOH) are as follows:

ESI-MS m/z: 474 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 24H), 2.05-2.10 (m, 1H), 3.59 (m, 1H), 5.10-5.14 (m, 1H).

Example 4

Preparation of Protopanoxadiol Derivative of Structural Formula (I) ($R_1$ is —OH, and $R_2$ is —$NH_2$)

3 g of the compound I ($R_1$ is —OH, and $R_2$ is —$NH_2$) from Example 3 was accurately weighed and dissolved in anhydrous tetrahydrofuran 50 ml. Lithium aluminum hydride 0.25 g was added with stirring, thereafter stirred at 80° C. for 3 h. After the completion of the reaction showed by TLC, the reaction solution was filtered through celite, the organic phase was concentrated to dryness, and silica gel column chromatography was performed using dichloromethane and methanol of 20:1-5:1 (volume ratio) as eluting agent, to obtain 1.2 g of compound (I) ($R_1$ is —OH, and $R_2$ is —$NH_2$) (purity: 95%).

The structure was determined by ESI-MS and NMR, and the determined physicochemical data of the compound of formula (I) ($R_1$ is —OH, and $R_2$ is —$NH_2$) are as follows:

ESI-MS m/z: 460.3 (M+H)$^{-1}$H NMR (300 MHz, CDCl$_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 25H), 2.51-2.55 (m, 1H), 3.59 (m, 1H), 5.10-5.14 (m, 1H).

Example 5

Preparation of Protopanoxadiol Derivative of Structural Formula (I) ($R_1$ and $R_2$ are =NOH)

10 g of Adama-20S-24(R,S)-epoxy-3β,12β,25-triol (Shanghai Innovative Research Center of Traditional Chinese Medicine) was accurately weighed, and dissolved in anhydrous dichloromethane 250 ml. PDC 20 g was added with stirring thereafter stirred at room temperature for 24 h. After the completion of the reaction, the reaction solution was filtered through celite, the organic phase was concentrated to dryness, and gel column chromatography was performed using ethyl acetate and petroleum ether of 1:10-1:5 (volume ratio) as eluting agent, to obtain 6 g of compound IV (purity: 95%), Compound IV The structure was determined by ESI-MS and NMR, and the determined physicochemical data of the compound of formula (IV) are as follows:

ESI-MS m/z: 473.47 (M+H)⁻ ¹H NMR (300 MHz, CDCl₃): δ 0.77 (s, 3H), 0.85 (s, 3H), 0.90 (s, 3H), 0.97 (s, 3H), 1.10 (s, 3H), 1.27 (s, 3H), 1.28 (s, 3H), 1.30-2.23 (m, 23H), 2.85-2.95 (m, 2H), 3.84 (m, 1H).

5 g of the compound IV was accurately weighed and dissolved in anhydrous methanol 100 ml. Triethylamine 2.8 g and hydroxylamine hydrochloride 2.0 g were added with stirring. The solid began to separate out after stirring at room temperature for 24 h. The reaction solution was filtered with filter paper after the reaction was completed, and dried to obtain 5.0 g of compound (II) ($R_1$ and $R_2$ are =NOH) (purity: 95%).

The structure was determined by ESI-MS and NMR, and the determined physicochemical data of the compound of formula (II) ($R_1$ and $R_2$ are =NOH) were as follows:

ESI-MS m/z: 503.35 (M+H)⁻ ¹H NMR (300 MHz, CDCl₃): δ 0.77 (s, 3H), 0.85 (s, 3H), 0.90 (s, 3H), 0.97 (s, 3H), 1.10 (s, 3H), 1.27 (s, 3H), 1.28 (s, 3H), 1.30-2.23 (m, 23H), 3.01-3.09 (d, 2H), 3.84 (m, 1H).

Example 6

Preparation of Protopanoxadiol Derivative of Structural Formula (II) ($R_1$ and $R_2$ are —NH₂)

3 g of the compound II ($R_1$ and $R_2$ are =NOH) from Example 5 was accurately weighed and dissolved in anhydrous tetrahydrofuran 50 ml. Lithium aluminum hydride 0.5 g was added with stirring, thereafter stirred at 80° C. for reaction for 3 h. After the completion of the reaction showed by TLC, the reaction solution was filtered through celite, the organic phase was concentrated to dryness, and silica gel column chromatography was performed using dichloromethane and methanol of 20:1-5:1 (volume ratio) as eluting agent, to obtain 1.3 g of compound II ($R_1$ and $R_2$ are —NH₂) (purity: 95%)

The structure was determined by ESI-MS and NMR, and the determined physicochemical data of the compound of formula (II) ($R_1$ and $R_2$ are —NH₂) are as follows:

ESI-MS m/z: 475.47 (M+H)⁻ ¹H NMR (300 MHz, CDCl₃): δ 0.77 (s, 3H), 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.23 (m, 22H), 3.40 (d, 1H), 3.52 (m, 1H), 3.84 (d, 1H).

Example 7

Preparation of Protopanoxadiol Derivative of Structural Formula (II) ($R_1$ is —OH, and $R_2$ is =NOH)

10 g of Adama-20S-24(R,S)-epoxy-3β,12β,25-triol (Shanghai Innovative Research Center of Traditional Chinese Medicine) was accurately weighed, and dissolved in anhydrous dichloromethane 250 ml. PDC 10 g was added with stirring, thereafter stirred at room temperature for 24 h. After the completion of the reaction, the reaction solution was filtered through celite, the organic phase was concentrated to dryness, and silica gel column chromatography was performed using ethyl acetate and petroleum ether of 1:10-1:5 (volume ratio) as eluting agent, to obtain 4 g of compound VI (purity: 95%), Compound VI The structure was determined by ESI-MS and NMR, and the determined physicochemical data of the compound of formula (VI) are as follows:

ESI-MS m/z: 475.47 (M+H)⁻ ¹H NMR (300 MHz, CDCl₃): δ 0.77 (s, 3H), 0.85 (s, 3H), 0.90 (s, 3H), 0.97 (s, 3H), 1.10 (s, 3H), 1.27 (s, 3H), 1.28 (s, 3H), 1.30-2.23 (m, 25H), 3.59 (m, 1H), 3.84 (m, 1H).

5 g of the compound VI was accurately weighed and dissolved in anhydrous methanol 100 ml. Triethylamine 1.4 g and hydroxylamine hydrochloride 1.0 g are added with stirring. The solid began to separate out after stirring at room temperature for 24 h. The reaction solution was filtered with filter paper after the reaction was completed, and dried to obtain 4.0 g of compound II ($R_1$ is —OH, and $R_2$ is =NOH) (purity: 95%).

The structure was determined by ESI-MS and NMR, and the determined physicochemical data of the compound of formula (II) ($R_1$ is —OH, and $R_2$ is =NOH) are as follows:

ESI-MS m/z: 490.02 (M+H)⁻ ¹H NMR (300 MHz, CDCl₃): δ 0.77 (s, 3H), 0.85 (s, 3H), 0.90 (s, 3H), 0.97 (s, 3H), 1.10 (s, 3H), 1.27 (s, 3H), 1.28 (s, 3H), 1.30-2.61 (m, 23H), 3.15-3.17 (m, 1H), 3.84 (m, 1H).

Example 8

Preparation of Protopanoxadiol Derivative of Structural Formula (II) ($R_1$ is —OH, and $R_2$ is —NH₂)

3 g of the compound II ($R_1$ is —OH, and $R_2$ is =NOH) from Example 7 was accurately weighed and dissolved in anhydrous tetrahydrofuran 50 ml. Lithium aluminum hydride 0.25 g was added with stirring, thereafter stirred at 80° C. for reaction for 3 h. After the completion of the reaction showed by TLC, the reaction solution was filtered through celite, the organic phase was concentrated to dryness, and silica gel column chromatography was performed using dichloromethane and methanol of 20:1-5:1 (volume ratio) as eluting agent, to obtain 0.82 g of compound II ($R_1$ is —OH, and $R_2$ is —NH₂) (purity: 95%)

The structure was determined by ESI-MS and NMR, and the determined physicochemical data of the compound of formula (II) ($R_1$ is —OH, and $R_2$ is —NH₂) are as follows:

ESI-MS m/z: 475.47 (M+H)⁻ ¹H NMR (300 MHz, CDCl₃): δ 0.77 (s, 3H), 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.23 (m, 22H), 2.52 (m, 1H), 3.38 (d, 1H), 3.52 (m, 1H), 3.84 (d, 1H).

Example 9

Preparation of Protopanoxadiol Derivative of Structural Formula (I) ($R_1$ and $R_2$ are =NOH)

10 g of 20(S)-protopanoxadiol (Shanghai Innovative Research Center of Traditional Chinese Medicine) was accurately weighed, and dissolved in anhydrous dichloromethane 250 ml. Dess-Martin reagent 20 g was added with stirring, thereafter stirred at room temperature for 24 h. After the completion of the reaction, the reaction solution was quenched with water, the organic phase was concentrated to dryness, and silica gel column chromatography was performed using ethyl acetate and petroleum ether of 1:10-1:5 (volume ratio) as eluting agent, to obtain 5.2 g of compound III (purity: 97%), Compound III The structure was determined by ESI-MS and NMR, and the determined physicochemical data of the compound of formula (III) are as follows:

ESI-MS m/z: 457.4 $(M+H)^{-1}$H NMR (300 MHz, $CDCl_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 24H), 2.85-2.95 (m, 1H), 5.10-5.14 (m, 1H).

5 g of the compound III was accurately weighed and dissolved in anhydrous methanol 100 ml. Triethylamine 2.77 g and hydroxylamine hydrochloride 1.9 g were added with stirring. The solid began to separate out after stirring at room temperature for 24 h. The reaction solution was filtered with filter paper after the reaction was completed, and dried to obtain 4.8 g of compound (I) ($R_1$ and $R_2$ are =NOH) (purity: 95%).

The structure was determined by ESI-MS and NMR, and the determined physicochemical data of the compound of formula (I) ($R_1$ and $R_2$ are =NOH) are as follows:

ESI-MS m/z: 487.4 $(M+H)^{-1}$H NMR (300 MHz, $CDCl_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 23H), 2.85-2.95 (m, 2H), 5.10-5.14 (m, 1H).

Example 10

Preparation of Protopanoxadiol Derivative of Structural Formula (I) ($R_1$ and $R_2$ are —$NH_2$)

3 g of the compound I ($R_1$ and $R_2$ are —$NH_2$) from Example 1 was accurately weighed and dissolved in n-propanol 50 ml. Sodium 1.7 g was added with stirring. The reaction was performed for 3 h with stirring at 100° C. The reaction was quenched after TLC showed that the reaction was completed. The organic phase was concentrated to dryness, and silica gel column chromatography was performed using dichloromethane and methanol of 20:1-5:1 (volume ratio) as eluting agent, to obtain 1.5 g of compound I ($R_1$ and $R_2$ are —$NH_2$) (purity: 96%)

The structure was determined by ESI-MS and NMR, and the determined physicochemical data of the compound of formula (I) ($R_1$ and $R_2$ are —$NH_2$) are as follows:

ESI-MS m/z: 459.3 $(M+H)^{-1}$H NMR (300 MHz, $CDCl_3$): δ 0.85 (s, 3H), 0.90 (s, 3H), 0.97 (s, 3H), 0.98 (s, 3H), 1.10 (s, 3H), 1.27 (s, 3H), 1.28 (s, 3H), 1.30-2.61 (m, 25H), 3.09 (m, 1H), 3.39 (m, 1H), 5.10-5.14 (m, 1H).

Example 11

10 g of the compound I (any compound I obtained in above Examples 1-4 and 9-10) was mixed well with appropriate amount of lactose and granulated using 70% ethanol as binder. The resultant particle was filled into capsules. Each capsule contains 20 mg of the compound I.

Example 12

10 g of the compound I (any compound I obtained in above Examples 1-4 and 9-10) was mixed well with appropriate amount of lactose granulated using 70% ethanol as binder, dried, and compressed to obtain tables after adding appropriate amount of magnesium stearate. Each tablet contains 50 mg of the compound I.

Example 13

Appropriate amount of emulsifier (Tween or Span, etc.) was dissolved in water, followed by adding the compound I (any compound I obtained in above Examples 1-4 and 9-10), grinding into primary emulsion, and adding water to 1,000 ml to obtain an oral solution.

Example 14

Appropriate amount of emulsifier (Tween or Span, etc.) was dissolved in injectable water, followed by adding the compound I (any compound I obtained in above Examples 1-4 and 9-10), filtering, sterilizing and encapsulating to obtain an injection solution.

The preparation method for corresponding preparations containing the compound II is the same as Examples 11-14.

The purpose of the experimental examples is to investigate the anti-depression activity of the protopanoxadiol derivatives of the present invention.

Experimental Example 1

Mice Forced Swimming Method Acquired Despair Depression Model Test (1) Experimental Animals Variety: Clean Kunming mice; Sex: male; Body Weight: 18-22 g.

Source: Shanghai SLAC Laboratory Animal Co., Ltd., License No.: SCXK (Shanghai) 2007-0005.

(2) Drugs

20(S)-protopanoxadiol, compounds I and II (being compounds of Examples 1-8 respectively), venlafaxine hydrochloride Configuration: the powder was dissolved in a blank solvent, with dissolution being assisted by ultrasound.

(3) Experimental Methods and Results

Figure 1:
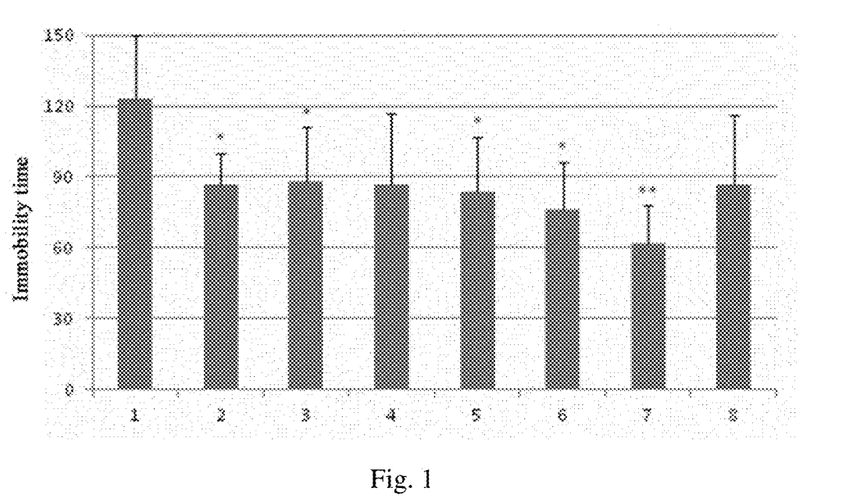
FIGS. 1-8 shows effects of the protopanoxadiol derivatives of Experimental Example 1 according to the present invention on mice forced swimming test; wherein 1: blank solvent group; 2: venlafaxine group (32 mg/kg); 3: protopanoxadiol group (0.75 mg/kg); 4: Examples 1-8 (0.15 mg/kg); 5: Examples 1-8 (0.375 mg/kg); 6: Examples 1-8 (0.75 mg/kg); 7. Examples 1-8 (1.5 mg/kg); 8: Examples 1-8 (3 mg/kg); as compared to the blank solvent group, *$P<0.05$, **$P<0.01$.
Figure 2:
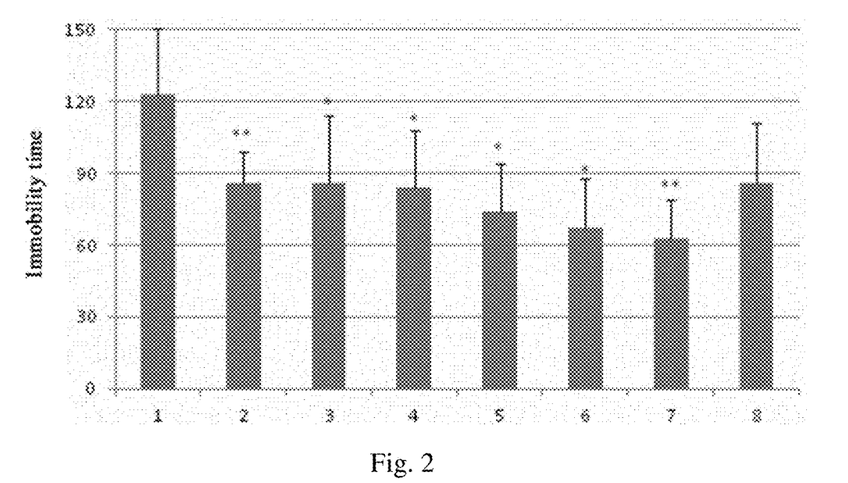
Figure 3:
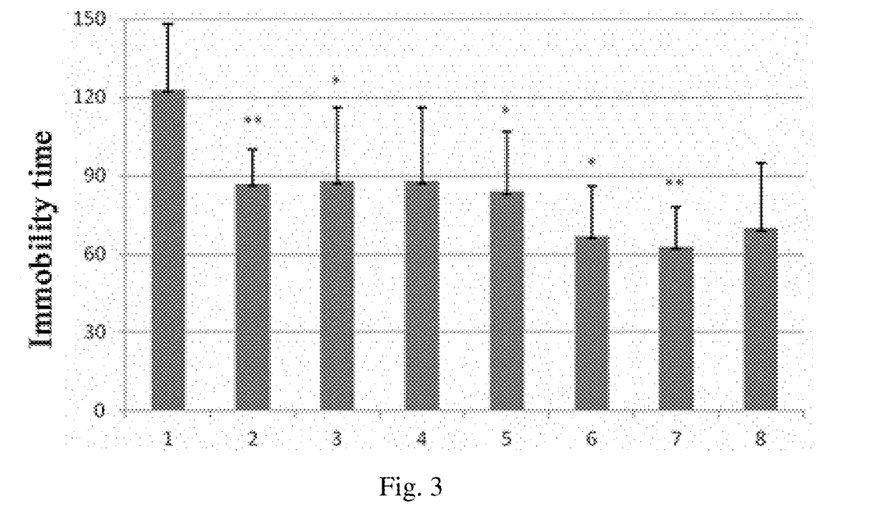
Figure 4:
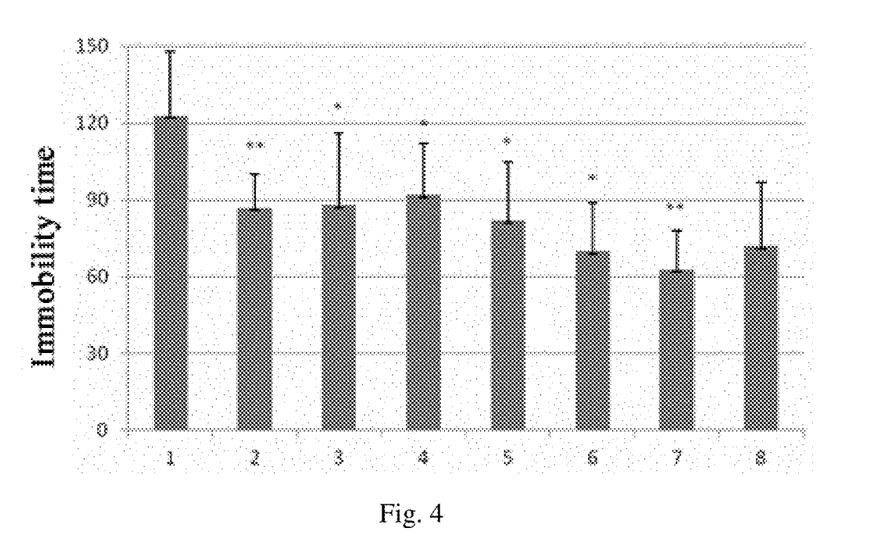
Figure 5:
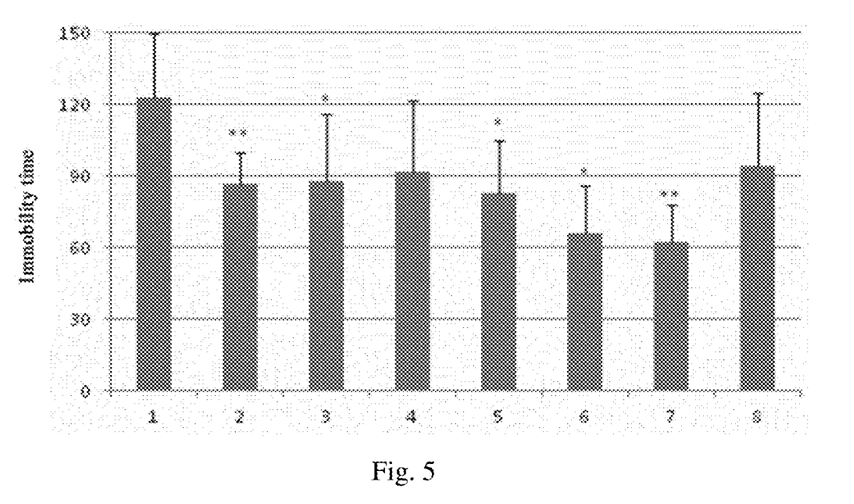
Figure 6:
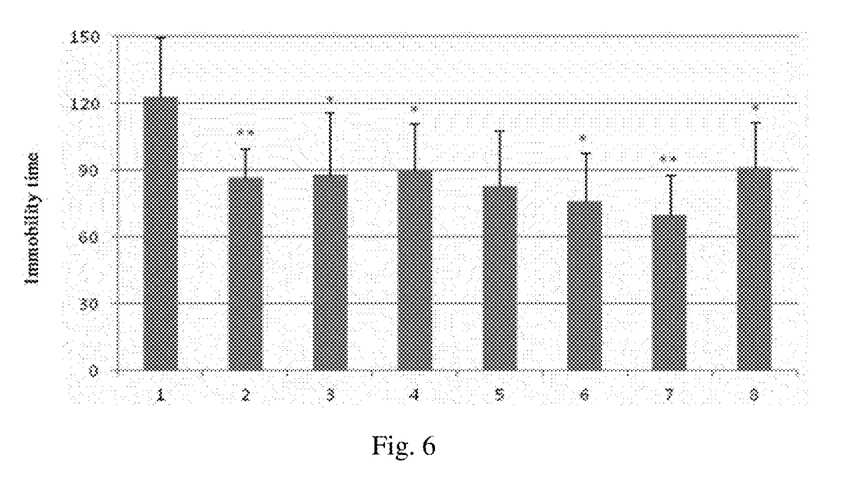
Figure 7:
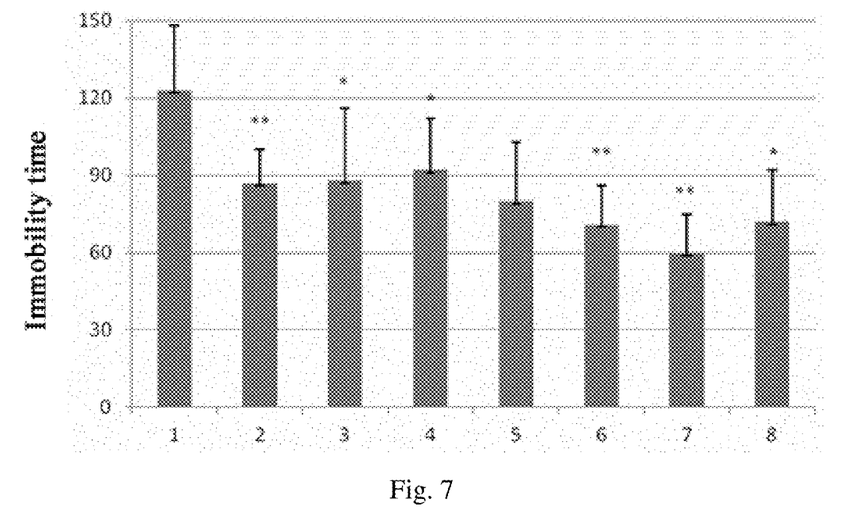
Figure 8:
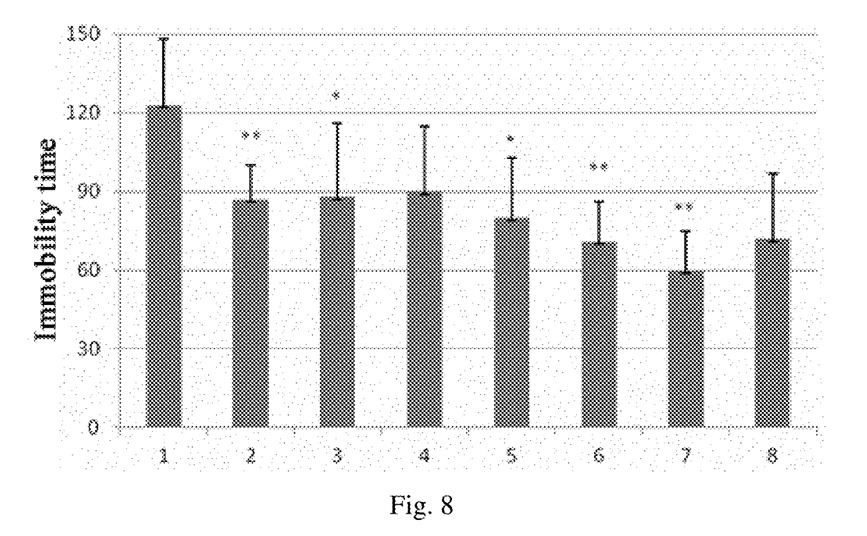

All mice, which were not pre-screened, were grouped randomly, were injected according to the drugs and dosages listed in FIGS. 1-8 (FIGS. 1-8 correspond to drugs obtained in Examples 1-8 respectively, and the dosage forms of the venlafaxine group and 20(S)-protopanoxadiol group were both same) for 4 days, and then subjected to the forced swimming test. The duration time of swimming model was 6 min, the time when mice did not swim within the later 4 minutes is recorded, and the results were shown in FIGS. 1-8.

(4) Conclusion

The forced swimming model research in "acquired despair" test showed that the derivatives I and II both can significantly shorten the non-swimming time of mice at different dosages; and the used dosage of the derivatives is much lower than that of positive control venlafaxine, and at the same dosage (0.75 mg/kg), the activity of the derivatives is obviously stronger than that of 20(S)-protopanoxadiol.

Experimental Example 2

Mice Tail Suspension Method Acquired Despair Depression Model Test (1) Experimental Animals Variety: Clean ICR mice; Sex: male; Body Weight: 22-24 g.

Source: Shanghai SLAC Laboratory Animal Co., Ltd., License No.: SCXK (Shanghai) 2007-0005.

(2) Experimental Drugs and Instruments

20(S)-protopanoxadiol, compounds I and II (being compounds of Examples 1-8 respectively), venlafaxine hydrochloride Shanghai Mobile Datum Information Technology Co., Ltd provided a ZH-XWT type tail suspension test video analysis system.

(3) Experimental Methods and Results

Figure 9:
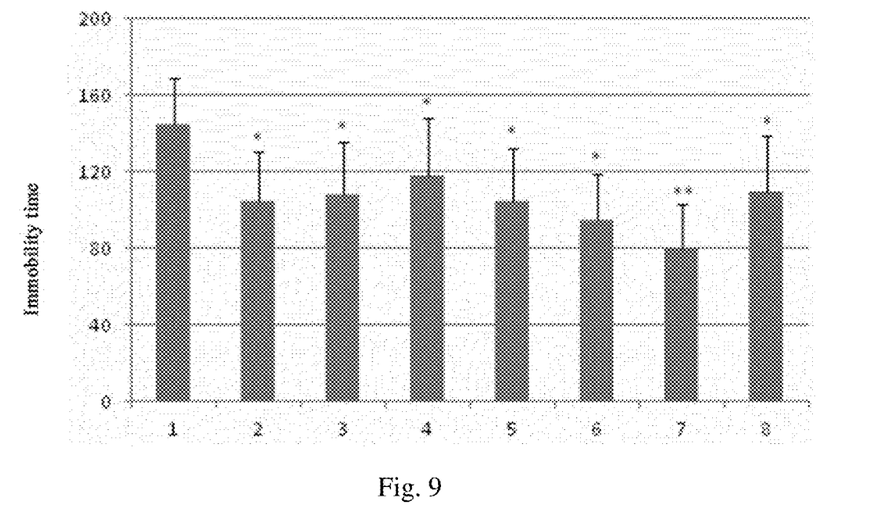
FIGS. 9-16 shows effects of the protopanoxadiol derivatives of Experimental Example 2 according to the present invention on mice tail suspension test; wherein 1: blank solvent group; 2: venlafaxine group (32 mg/kg); 3: protopanoxadiol group (0.75 mg/kg); 4: Examples 1-8 (0.15 mg/kg); 5: Examples 1-8 (0.375 mg/kg); 6: Examples 1-8 (0.75 mg/kg); 7. Examples 1-8 (1.5 mg/kg); 8: Examples 1-8 (3 mg/kg); as compared to the blank solvent group, *$P<0.05$, **$P<0.01$.
Figure 10:
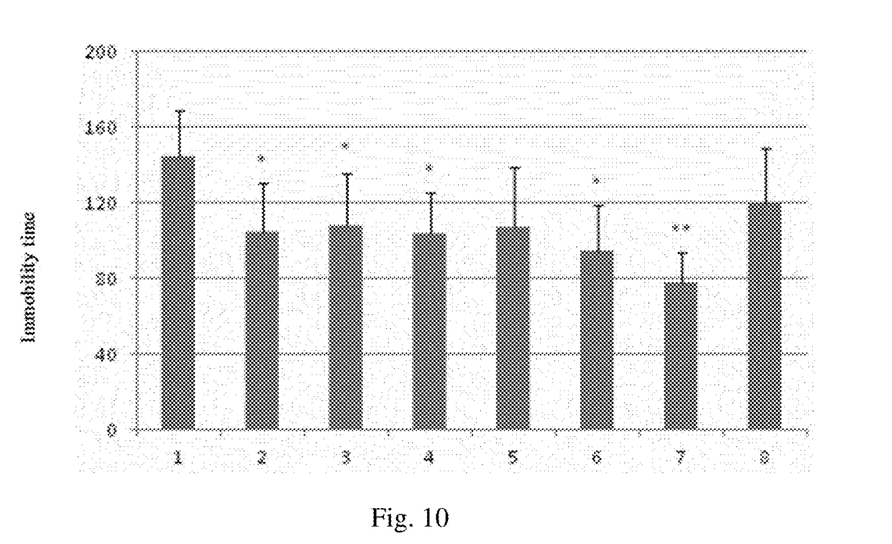
Figure 11:
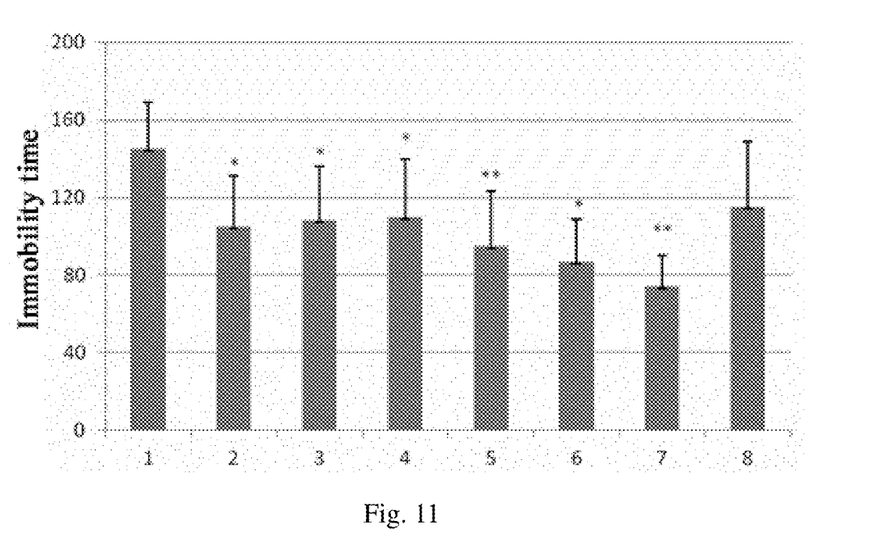
Figure 12:
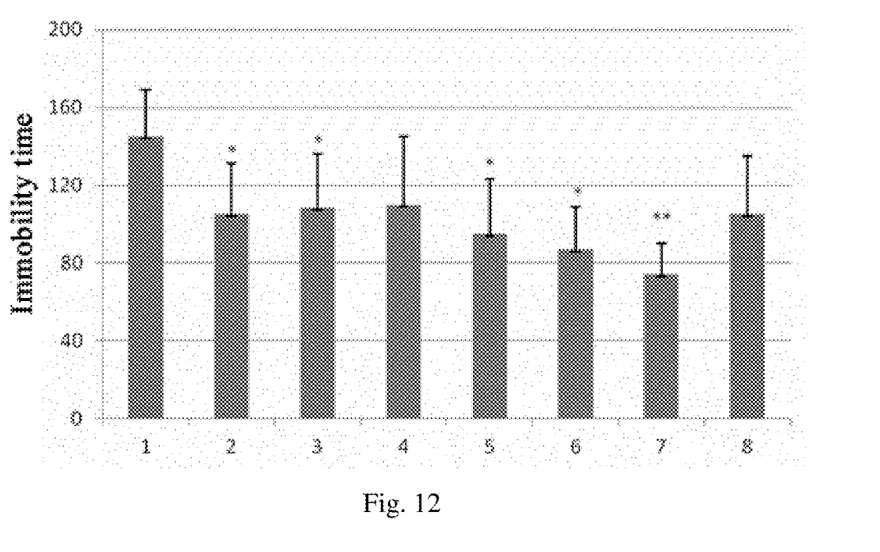
Figure 13:
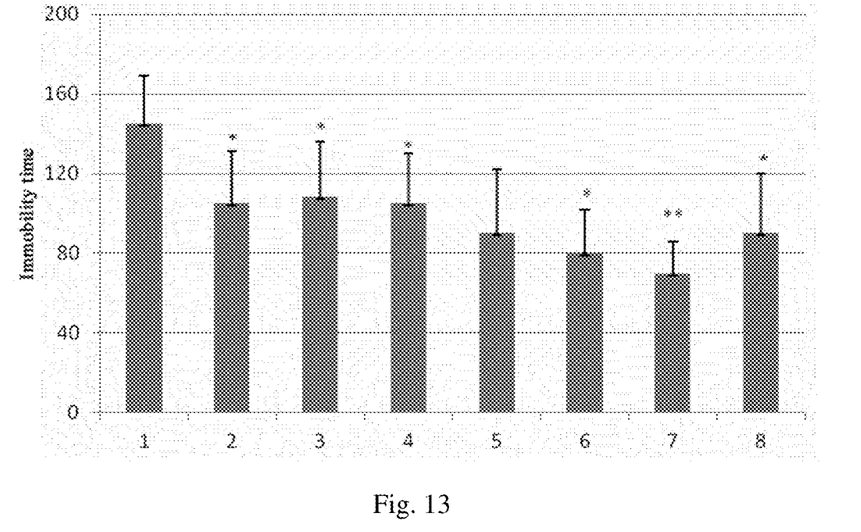
Figure 14:
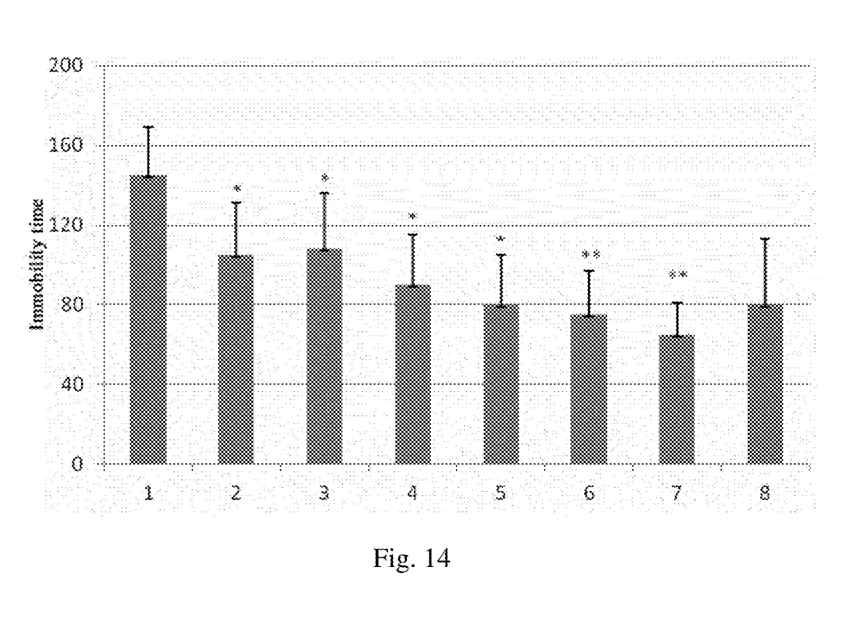
Figure 15:
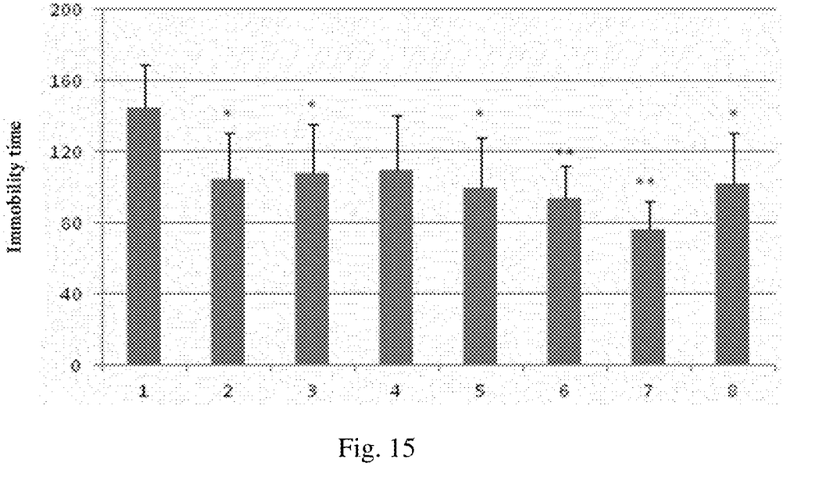
Figure 16:
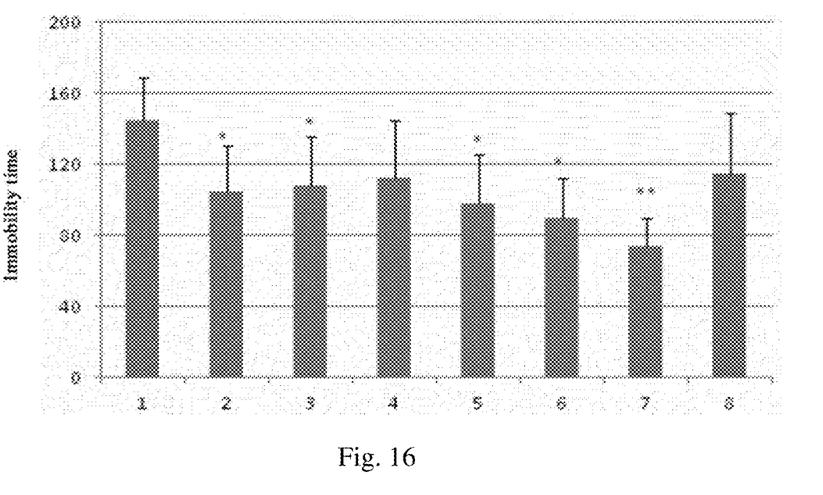

All mice, which were not pre-screened, were grouped randomly, were injected according to the drugs and dosages listed in FIGS. 9-16 (FIGS. 9-16 correspond to drugs obtained in Examples 1-8 respectively, and the dosage forms of the venlafaxine group and 20(S)-protopanoxadiol group were both same) for 4 days, and then subjected to the tail suspension test.

The method specifically comprises adhering the part of tails of mice 1 cm away from the tip of the tails to a PVC tube with a diameter of 1 cm with adhesive plaster, please note that the tails of the mice should not be twisted and folded then hanging the PVC tube to make the mouse hung down with head 5 cm away from a table, separating every two mice with a separating plate to make the two mice not disturb each other, observing accumulated immobility time of each mouse within 6 min (immobility index means the animal does not move any limbs except breathing), wherein the first 1 or 2 minutes are time for the mice to adapt, and recording the accumulated immobility time, absolute immobility time and struggling time of the mouse within the later 5 minutes by an instrument, please note that the environment for observation should be kept quiet, thus avoiding noise disturbance. The results were shown in FIGS. 9-16.

(4) Conclusion

The tail suspension model research in "acquired despair" test showed that the derivatives I and II both can significantly shorten the tail suspension immobility time of mice at different dosages; and the dosage of the derivatives is much lower than that of positive control venlafaxine, and at the same dosage (0.75 mg/kg), the activity of the derivatives is obviously stronger than that of 20(S)-protopanoxadiol.

Experimental Example 3

Rat Chronic Unpredictable Mild Stress Depression Model (CUMS) Test (1) Experimental Animals Variety: Wistar rats; Sex: male; Body Weight: 200 g.

Source: Shanghai SLAC Laboratory Animal Co., Ltd., License No.: SCXK (Shanghai) 2012-0002.

(2) Experimental Drugs and Instruments

Compounds I and II (being compounds of Examples 1 and 5 respectively), venlafaxine hydrochloride (3) Experimental Methods and Results Experimental method comprises starting CUMS program after adaptively breeding the rats for 1 week.

1) Sucrose preference experiment: all animals were fed with 1% sucrose water within the first 24 h; during the subsequent 24 h, all the animals were simultaneously fed with 1% sucrose water and common drinking water, then fasted with water deprivation for 23 h. Subsequently sucrose preference experiment was performed: simultaneously feeding the animals with 1% sucrose water and common drinking water, and measuring the drinking amounts of sucrose water and common drinking water for animals in 1 h by weighing the drinking water bottles. The animals were grouped evenly according to the animal body weight, liquid consumption amount and sucrose water consumption, and subjected to chronic unpredictable mild stress stimulation.

2) CUMS experiment: the rats were alternately given tens of stress stimulation factors each week, so that the rats cannot predict the stimulation duration of each stress factor and the stimulation to be given subsequently. The stimulation factor includes: flash stimulation, noise stimulation, rat cage inclination; and strange smell environment feeding, fasting, water deprivation.

3) Detection method comprising: detecting liquid consumption amount after food-fasting and water-deprivation for 21 h each week, recording the body weight, total liquid intake, water intake and sucrose water intake of each animal, and calculating sucrose water preference percentage (preference=(sucrose water intake/total liquid intake)×100%) and sucrose water consumption amount per gram of body weight of each rat.

The results are shown in the following table:

TABLE 1

Effect of each group on the sucrose water intake of CUMS rats
(n = 10, $\bar{x} \pm SD$)

| Group | Sucrose water intake percentage (%) | | | | |
|---|---|---|---|---|---|
| | Third week | Fourth week | Fifth week | Sixth week | Seventh week |
| Model group (blank solvent) | 0.76 ± 0.18 | 0.73 ± 0.11 | 0.64 ± 0.14 | 0.65 ± 0.15 | 0.62 ± 0.16 |
| Venlafaxine group 20 mg/kg | 0.81 ± 0.09 | 0.88 ± 0.05 | 0.83 ± 0.09** | 0.85 ± 0.06** | 0.84 ± 0.11** |
| Compound I 1.5 mg/kg | 0.76 ± 0.09 | 0.85 ± 0.09 | 0.87 ± 0.11** | 0.88 ± 0.15* | 0.89 ± 0.18* |
| Compound I 0.75 mg/kg | 0.77 ± 0.14 | 0.83 ± 0.18 | 0.82 ± 0.14** | 0.81 ± 0.13* | 0.80 ± 0.15* |
| Compound I 0.375 mg/kg | 0.82 ± 0.14 | 0.82 ± 0.16 | 0.70 ± 0.18 | 0.70 ± 0.15 | 0.69 ± 0.25 |
| Compound II 1.5 mg/kg | 0.87 ± 0.16 | 0.85 ± 0.18 | 0.86 ± 0.09** | 0.86 ± 0.16* | 0.88 ± 0.18** |
| Compound II 0.75 mg/kg | 0.76 ± 0.16 | 0.82 ± 0.10 | 0.81 ± 0.12** | 0.82 ± 0.13* | 0.81 ± 0.17* |
| Compound II 0.375 mg/kg | 0.80 ± 0.09 | 0.81 ± 0.05 | 0.78 ± 0.09 | 0.79 ± 0.06 | 0.77 ± 0.11 |

**$P < 0.01$;
*$P < 0.05$, as compared to the model group.

(4) Conclusion

It can be seen from table 1 that the rat sucrose preference degree (intake) of the model group showed progressive reduction;

For the venlafaxine group (20 mg/kg), the sucrose water intake of CUMS rats could be increased from the fourth week, and as compared to the model group, showed statistically significant difference ($P<0.01$) during the fifth week;

The compounds I and II (1.5 mg/kg and 0.75 mg/kg) showed a trend to increase the sucrose water intake of CUMS rats from the fourth week, and as compared to the model group, showed statistically significant difference ($P<0.01$ or $0.05$) after the fifth week; for the compounds (0.375 mg/kg), the effect was not significant; and similarly, the effective dosage of the model was much lower than the effective dosage of the positive control venlafaxine group.

Although the present invention has been described in detail using general description and specific embodiments above, it is obvious to a person skilled in the art to make some modifications and improvements based on the present invention. Hence these modifications and modifications made without deviating from the spirit of the present invention all belong to the protection scope of the present invention.

INDUSTRIAL APPLICABILITY

The present invention made structural modification on protopanoxadiol, to obtain various new compounds with unique structures, and it has been proved by in-vivo pharmacological experiments that these compounds have stronger anti-depression activity, can be used as the active ingredients in preparing drugs for preventing or treating depression mental diseases, and have wide application and development prospect.

What is claimed is:

1. A protopanoxadiol derivative represented by formula I or II:

(I)

(II)

Wherein, $R_1$ is —OH, =NOH or —NH$_2$;
$R_2$ is —OH, =NOH or —NH$_2$; and
$R_1$ and $R_2$ are not —OH simultaneously.

2. The protopanoxadiol derivative according to claim 1, wherein when $R_1$ is —OH, $R_2$ is =NOH or —NH$_2$.

3. The protopanoxadiol derivative according to claim 1, wherein $R_1$ and $R_2$ each independently is =NOH or —NH$_2$.

4. A method for preparing the protopanoxadiol derivative according to claim 1, comprising:
1) subjecting protopanoxadiol or Adama-20S-24(R,S)-epoxy-3β,12β,25-triol to oxidation reaction to obtain a monoxide or dioxide derivative respectively;
2) subjecting the monoxide or dioxide derivative obtained in step 1) and hydroxylamine hydrochloride to additional reaction or further reduction reaction to obtain a compound represented by formula (I) or (II);
wherein the dioxide derivative is:

Compound III

Compound IV and
the monoxide derivative is:

Compound V

Compound VI

5. The method according to claim 4, wherein the oxidant used during oxidation reaction in step 1) is selected from the group consisting of manganese dioxide, potassium permanganate, Dess-Martin reagent, PCC, PDC and Jones reagent.

6. The method according to claim 4, wherein the reductant used during reduction reaction in step 2) is selected from the group consisting of $NaBH_4$, $LiAlH_4$, Na/n-propanol and Zn/AcOH.

7. A pharmaceutical composition comprising the protopanoxadiol derivative of structural formula I or II according to claim 1.

8. The pharmaceutical composition according to claim 7, wherein the pharmaceutical composition is an oral preparation or injection preparation.

9. A method of treating a depression mental disease in a subject comprising administering the protopanoxadiol derivative according to claim 1 to the subject.

10. The method according to claim 9 wherein the depression mental disease is selected from the group consisting of paralepsy, recurrent depressive disorder, bipolar affective disorder and persistent mood disorder.

11. The pharmaceutical composition according to claim 8, wherein the oral preparation is a capsule, tablet, pill, or granule.

12. The protopanoxadiol derivative according to claim 1, wherein $R_1$ and $R_2$ are =NOH or —$NH_2$ simultaneously.

13. The protopanoxadiol derivative according to claim 1, wherein $R_1$ is —OH, and $R_2$ is =NOH or —$NH_2$.

14. The protopanoxadiol derivative according to claim 1, wherein when $R_2$ is —OH, $R_1$ is =NOH or —$NH_2$.

* * * * *